United States Patent
Kristen et al.

(10) Patent No.: US 6,828,454 B2
(45) Date of Patent: Dec. 7, 2004

(54) METAL COMPLEXES OF IMINOHYDROXAMIC ACIDS

(75) Inventors: Marc Oliver Kristen, Limburgerhof (DE); Peter Preishuber-Pflügl, Ludwigshafen (DE); Benno Bildstein, Innsbruck (AT); Alexander Krajete, Salzburg (AT)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/364,380

(22) Filed: Feb. 12, 2003

(65) Prior Publication Data

US 2003/0191255 A1 Oct. 9, 2003

(30) Foreign Application Priority Data

Feb. 13, 2002 (DE) .......................................... 102 06 113

(51) Int. Cl.⁷ ........................... C07F 15/02; C07F 15/04
(52) U.S. Cl. ....................... 556/138; 556/137; 556/146; 526/171; 526/172
(58) Field of Search ................................. 526/171, 172; 556/137, 148, 146

(56) References Cited

U.S. PATENT DOCUMENTS

2001/0025007 A1    9/2001   Ponasik, Jr. et al.

FOREIGN PATENT DOCUMENTS

| EP | 0 874 005 | 10/1998 |
|---|---|---|
| EP | 0 946 609 | 2/2002 |
| WO | WO 96/23010 | 8/1996 |
| WO | WO 98/27124 | 6/1998 |
| WO | WO 98/40420 | 9/1998 |

OTHER PUBLICATIONS

H. H. Brintzinger, et al., Angew. Chem. Int. Ed. Engl., vol., 34, pp. 1143–1170, "Stereospecific Olefin Polymerization with Chiral Metallocene Catalysts", 1995.

G. J. P. Britovsek, et al., Angew. Chem. Int. Ed., vol. 38, pp. 429–447, "The Search for New–Generation Olefin Polymerization Catalysts: Life Beyond Metallocenes", 1999.

Primary Examiner—Caixia Lu
(74) Attorney, Agent, or Firm—Oblon, Spivak, McClelland, Maier & Neustadt, P.C.

(57) ABSTRACT

Complexes of the formula I

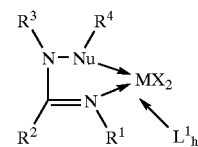

where M=Ni, Pd; process for preparing the metal complexes and the use of the complexes obtainable in this way for the polymerization and copolymerization of olefins, for example in suspension polymerization processes, gas-phase polymerization processes and bulk polymerization processes.

14 Claims, No Drawings

METAL COMPLEXES OF IMINOHYDROXAMIC ACIDS

The present invention relates to complexes of the formulae I,

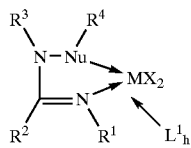

where the variables are defined as follows:

Nu is selected from among O, S, N—$R^{4*}$, P—$R^{4*}$,
M is selected from among Ni, Pd;
h is an integer from 0 to 4;
X are identical or different and are selected from among halogen, $C_1$–$C_8$-alkyl, $C_3$–$C_{12}$-cycloalkyl, $C_7$–$C_{13}$-aralkyl and $C_6$–$C_{14}$-aryl,
$R^1$, $R^4$, $R^{4*}$ are identical or different and are selected from among hydrogen
  $C_1$–$C_{18}$-alkyl, substituted or unsubstituted,
  $C_2$–$C_{18}$-alkenyl, substituted or unsubstituted, which has from one to 4 isolated or conjugated double bonds and is bound via a single bond;
  $C_3$–$C_{12}$-cycloalkyl, substituted or unsubstituted,
  $C_7$–$C_{13}$-aralkyl,
  $C_6$–$C_{14}$-aryl, unsubstituted or substituted by one or more identical or different substituents selected from among
    $C_1$–$C_{18}$-alkyl, substituted or unsubstituted,
    $C_2$–$C_{18}$-alkenyl, substituted or unsubstituted,
    $C_3$–$C_{12}$-cycloalkyl,
    $C_7$–$C_{13}$-aralkyl,
    $C_6$–$C_{14}$-aryl,
    halogen,
    $C_1$–$C_6$-alkoxy, substituted or unsubstituted,
    $C_6$–$C_{14}$-aryloxy,
    $SiR^5R^6R^7$ and O—$SiR^5R^6R^7$;
  five- to six-membered nitrogen-containing heteroaryl radicals which may be unsubstituted or substituted by one or more identical or different substituents selected from among
    $C_1$–$C_{18}$-alkyl, substituted or unsubstituted,
    $C_2$–$C_{18}$-alkenyl, substituted or unsubstituted,
    $C_3$–$C_{12}$-cycloalkyl,
    $C_7$–$C_{13}$-aralkyl,
    $C_6$–$C_{14}$-aryl,
    halogen,
    $C_1$–$C_6$-alkoxy,
    $C_6$–$C_{14}$-aryloxy,
    $SiR^5R^6R^7$ and O—$SiR^5R^6R^7$;
  and are bound via a single bond;
$R^2$ is $C_6$–$C_{14}$-aryl, unsubstituted or substituted by one or more identical or different substituents, or a five- to six-membered nitrogen-containing heteroaryl radical, unsubstituted or substituted by one or more identical or different substituents, where the substituents are as defined above;
$R^3$ is $C_1$–$C_8$-alkyl, $C_2$–$C_{18}$-alkenyl, substituted or unsubstituted and having from one to 4 isolated or conjugated double bonds, $C_3$–$C_{12}$-cycloalkyl, substituted or unsubstituted, $C_7$–$C_{13}$-aralkyl, $C_6$–$C_{14}$-aryl, unsubstituted or substituted by one or more identical or different substituents, or a five- to six-membered nitrogen-containing heteroaryl radical, unsubstituted or substituted by one or more identical or different substituents, where the substituents are as defined above;
  where adjacent radicals $R^1$ to $R^4$ may be joined to one another to form a 5- to 12-membered ring which may in turn bear substituents selected from among $C_1$–$C_8$-alkyl, substituted or unsubstituted, $C_2$–$C_8$-alkenyl, substituted or unsubstituted and having from one to 4 isolated or conjugated double bonds, $C_3$–$C_{12}$-cycloalkyl, substituted or unsubstituted, $C_7$–$C_{13}$-aralkyl and $C_6$–$C_{14}$-aryl;
$L^1$ is an uncharged, organic or inorganic ligand,
$R^5$ to $R^7$ are identical or different and are selected from among hydrogen, $C_1$–$C_8$-alkyl, $C_3$–$C_{12}$-cycloalkyl, $C_7$–$C_{13}$-aralkyl and $C_6$–$C_{14}$-aryl.

The present invention further provides a process for the polymerization of olefins using complexes of the formula I.

Polymers and copolymers of olefins are of great economic importance because the monomers are readily available in large quantities and because the polymers can be varied within a wide range by variation of the production process or the processing parameters. In the production process, the catalyst used is of particular importance. Apart from Ziegler-Natta catalysts, various types of single-site catalysts are of increasing importance, with metals which have been examined in detail as central atoms being not only Zr as in metallocene catalysts (H.-H. Brintzinger et al., *Angew. Chem.* 1995, 107, 1255) but also Ni or Pd (WO 96/23010) or Fe and Co (e.g. WO 98/27124). The complexes of Ni, Pd, Fe and Co are also referred to as complexes of late transition metals.

Metallocene catalysts have disadvantages for industrial use. The most frequently used metallocenes, namely zirconocenes and hafnocenes, are sensitive to hydrolysis. In addition, most metallocenes are sensitive toward many catalyst poisons such as alcohols, ethers or CO, which makes it necessary for the monomers to be carefully purified.

While Ni or Pd complexes (WO 96/23010) catalyst the formation of highly branched polymers which are of little commercial interest, the use of Fe or Co complexes leads to the formation of highly linear polyethylene with very small proportions of comonomer.

EP-A 0 874 005 discloses further polymerization-active complexes. These are preferably Ti complexes with salicylaldimine ligands. These, too, bear phenyl substituents or substituted phenyl substituents on the aldimine nitrogen (pages 18–23) or else the aldimine nitrogen is incorporated in a 6-membered ring (pages 31–32). However, they generally produce low molecular weight polyethylenes which are of limited suitability as materials. Furthermore, in all the ligands disclosed in EP-A 0 874 005, the oxygen atom is part of a phenolic system, which restricts the choice of readily available starting materials.

U.S. Pat. No. 2001/0025007 discloses compounds of the formulae A and B

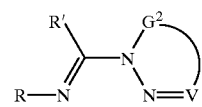

-continued

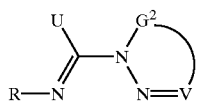
B and their use as catalysts for the polymerization of olefins, where $G^2$, R and R' are hydrocarbon radicals, U is a group such as alkoxy and V is selected from among CR, N and $PR_2$. However, the synthesis of such complexes A and B is rather complicated. In addition, the process engineering parameters of the complexes A and B are capable of improvement.

As G. J. P. Britovsek et al. in *Angew. Chem.* 1999, 111, 448, and *Angew. Chem. Int. Ed. Engl.* 1999, 38, 428, show, the search for very versatile polymerization-active complexes continues to be of importance because of the great commercial importance of polyolefins. There is interest in finding polymerization-active complexes which have a particularly advantageous property profile in process engineering terms.

It is an object of the invention
- to provide new complexes which are suitable for the polymerization of olefins to form high molecular weight polymers;
- to provide a process for preparing the complexes of the present invention;
- to provide a process for the polymerization or copolymerization of olefins using the complexes of the present invention;
- to provide supported catalysts for the polymerization of olefins and also a process for preparing the supported catalysts of the present invention using the complexes of the present invention;
- to polymerize and copolymerize olefins using the supported catalysts of the present invention.

We have found that this object is achieved by means of complexes which have the structures of the formula I defined at the outset.

In formula I, the variables are defined as follows:

Nu is selected from among O, S, N—$R^{4*}$ and P—$R^{4*}$, with oxygen and N—$R^{4*}$ being preferred;
M is selected from among Ni and Pd in the oxidation state +2, particularly preferably Ni;
h is an integer from 0 to 4, preferably 0;
X are identical or different and are selected from among
  halogen, such as fluorine, chlorine, bromine and iodine, preferably chlorine and bromine and particularly preferably chlorine;
  $C_1$–$C_8$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl and n-octyl; preferably $C_1$–$C_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably $C_1$–$C_4$-alkyl such as methyl, ethyl, n-propyl, isopropyl, n-butyl, isobutyl, sec-butyl and tert-butyl;
  $C_3$–$C_{12}$-cycloalkyl, such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;
  $C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl; and
  $C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl.
X is preferably halogen.
$R^1$, $R^4$ and $R^{4*}$ are identical or different and are selected from among
  hydrogen,
  $C_1$–$C_{18}$-alkyl groups, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-decyl, n-dodecyl and n-octadecyl; preferably $C_1$–$C_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl and n-decyl, particularly preferably $C_1$–$C_4$-alkyl such as methyl, ethyl, n-propyl, isopropyl, n-butyl, isobutyl, sec-butyl and tert-butyl;
  examples of substituted $C_1$–$C_{18}$-alkyl groups are: monohalogenated or polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;
  $C_2$–$C_{18}$-alkenyl which has from one to 4 isolated or conjugated double bonds and is bound via a single bond, for example vinyl, 1-allyl, 3-allyl, ω-butenyl, ω-pentenyl, ω-hexenyl, 1-cis-buta-1,3-dienyl and 1-cis-hexa-1,5-dienyl;
  examples of substituted $C_2$–$C_{18}$-alkenyl groups are: isopropenyl, 1-isoprenyl, α-styryl, β-styryl, 1-cis-1,2-phenylethenyl or 1-trans-1,2-phenylethenyl;
  $C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;
  examples of substituted cycloalkyl groups are: 2-methylcyclopentyl, 3-methylcyclopentyl, cis-2,4-dimethylcyclopentyl, trans-2,4-dimethylcyclopentyl, cis-2,5-dimethylcyclopentyl, trans-2,5-dimethylcyclopentyl, 2,2,5,5-tetramethylcyclopentyl, 2-methylcyclohexyl, 3-methylcyclohexyl, 4-methylcyclohexyl, cis-2,6-dimethylcyclohexyl, trans-2,6-dimethylcyclohexyl, cis-2,6-diisopropylcyclohexyl, trans-2,6-diisopropylcyclohexyl, 2,2,6,6-tetramethylcyclohexyl, 2-methoxycyclopentyl, 2-methoxycyclohexyl, 3-methoxycyclopentyl, 3-methoxycyclohexyl, 2-chlorocyclopentyl, 3-chlorocyclopentyl, 2,4-dichlorocyclopentyl, 2,2,4,4-tetrachlorocyclopentyl, 2-chlorocyclohexyl, 3-chlorocyclohexyl, 4-chlorocyclohexyl, 2,5-dichlorocyclohexyl, 2,2,6,6-tetrachlorocyclohexyl, 2-thiomethylcyclopentyl, 2-thiomethylcyclohexyl, 3-thiomethylcyclopentyl, 3-thiomethylcyclohexyl and further derivatives;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

$C_6$–$C_{14}$-aryl such as phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, substituted by one or more identical or different substituents selected from among $C_1$–$C_{18}$-alkyl groups, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl n-octyl, n-decyl, n-dodecyl and n-octadecyl; preferably $C_1$–$C_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl and n-decyl, particularly preferably $C_1$–$C_4$-alkyl such as methyl, ethyl, n-propyl, isopropyl, n-butyl, isobutyl, sec-butyl and tert-butyl;

examples of substituted $C_1$–$C_8$-alkyl groups are: mono-halogenated or polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

$C_2$–$C_{18}$-alkenyl having from one to 4 isolated or conjugated double bonds, for example vinyl, 1-allyl, 3-allyl, ω-butenyl, ω-pentenyl, ω-hexenyl, 1-cis-buta-1,3-dienyl and 1-cis-hexa-1,5-dienyl;

examples of substituted $C_2$–$C_{18}$-alkenyl groups are: isoprenyl, 1-isoprenyl, α-styryl, β-styryl, 1-cis-1, 2-phenylethenyl and 1-trans-1,2-phenylethenyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl and 2-naphthyl, particularly preferably phenyl;

halogen, for example fluorine, chlorine, bromine and iodine, particularly preferably fluorine and chlorine;

$C_1$–$C_6$-alkoxy groups such as methoxy, ethoxy, n-propoxy, isopropoxy, n-butoxy, isobutoxy, sec-butoxy, tert-butoxy, n-pentoxy, isopentoxy, n-hexoxy and isohexoxy, particularly preferably methoxy, ethoxy, n-propoxy and n-butoxy;

$C_6$–$C_{14}$-aryloxy groups such as phenoxy, ortho-cresyloxy, meta-cresyloxy, para-cresyloxy, α-naphthoxy, β-naphthoxy and 9-anthryloxy;

silyl groups $SiR^5R^6R^7$, where $R^5$ to $R^7$ are selected independently from among hydrogen, $C_1$–$C_8$-alkyl groups, the benzyl radical and $C_6$–$C_{14}$-aryl groups; preference is given to the trimethylsilyl, triethylsilyl, triisopropylsilyl, diethylisopropylsilyl, dimethylhexylsilyl, tert-butyldimethylsilyl, tert-butyldiphenylsilyl, tribenzylsilyl, triphenylsilyl and tri-para-xylylsilyl groups; particular preference is given to the trimethylsilyl group and the tert-butyldimethylsilyl group;

silyloxy groups $OSiR^5R^6R^7$, where $R^5$ to $R^7$ are selected independently from among hydrogen, $C_1$–$C_8$-alkyl groups, the benzyl radical and $C_6$–$C_{14}$-aryl groups; preference is given to the trimethylsilyloxy, triethylsilyloxy, triisopropylsilyloxy, diethylisopropylsilyloxy, dimethylhexylsilyloxy, tert-butyldimethylsilyloxy, tert-butyldiphenylsilyloxy, tribenzylsilyloxy, triphenylsilyloxy and tri-para-xylylsilyloxy groups; particular preference is given to the trimethylsilyloxy group and the tert-butyldimethylsilyloxy group;

five- to six-membered nitrogen-containing heteroaryl radicals bound via a single bond, for example N-pyrrolyl, pyrrol-2-yl, pyrrol-3-yl, N-imidazolyl, 2-imidazolyl, 4-imidazolyl, 1,2,4-triazol-3-yl, 1,2,4-triazol-4-yl, 2-pyridyl, 3-pyridyl, 4-pyridyl, 3-pyridazinyl, 4-pyridazinyl, 2-pyrimidinyl, 4-pyrimidinyl, 5-pyrimidinyl, N-indolyl and N-carbazolyl;

five- to six-membered nitrogen-containing heteroaryl radicals such as N-pyrrolyl, pyrrol-2-yl, pyrrol-3-yl, N-imidazolyl, 2-imidazolyl, 4-imidazolyl, 1,2,4-triazol-3-yl, 1,2,4-triazol-4-yl, 2-pyridyl, 3-pyridyl, 4-pyridyl, 3-pyridazinyl, 4-pyridazinyl, 2-pyrimidinyl, 4-pyrimidinyl, 5-pyrimidinyl, N-indolyl and N-carbazolyl, which are bound via a single bond and are substituted by one or more identical or different substituents selected from among $C_1$–$C_{18}$-alkyl groups, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl n-octyl, n-decyl, n-dodecyl and n-octadecyl; preferably $C_1$–$C_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl and n-decyl, particularly preferably $C_1$–$C_4$-alkyl such as methyl, ethyl, n-propyl, isopropyl, n-butyl, isobutyl, sec-butyl and tert-butyl;

examples of substituted $C_1$–$C_{18}$-alkyl groups are: monohalogenated or polyhalogenated $C_1$–$C_8$-alkyl groups such as fluoromethyl, difluoromethyl, trifluoromethyl, chloromethyl, dichloromethyl, trichloromethyl, bromomethyl, dibromomethyl, tribromomethyl, pentafluoroethyl, perfluoropropyl and perfluorobutyl, particularly preferably fluoromethyl, difluoromethyl, trifluoromethyl and perfluorobutyl;

$C_2$–$C_{18}$-alkenyl which has from one to 4 isolated or conjugated double bonds, for example vinyl, 1-allyl, 3-allyl, ω-butenyl, ω-pentenyl, ω-hexenyl, 1-cis-buta-1,3-dienyl and 1-cis-hexa-1,5-dienyl;

examples of substituted $C_2$–$C_{18}$-alkenyl groups are: isoprenyl, 1-isoprenyl, α-styryl, β-styryl, 1-cis-1,2-phenylethenyl or 1-trans-1,2-phenylethenyl;

$C_3$–$C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl and cycloheptyl;

$C_7$–$C_{13}$-aralkyl, preferably $C_7$–$C_{12}$-phenylalkyl such as benzyl, 1-phenethyl, 2-phenethyl, 1-phenylpropyl, 2-phenylpropyl, 3-phenylpropyl, neophyl (1-methyl-1-phenylethyl), 1-phenylbutyl, 2-phenylbutyl, 3-phenylbutyl and 4-phenylbutyl, particularly preferably benzyl;

$C_6$–$C_{14}$-aryl, for example phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl, preferably phenyl, 1-naphthyl und 2-naphthyl, particularly preferably phenyl;

halogen, for example fluorine, chlorine, bromine and iodine, particularly preferably fluorine and chlorine;

$C_1$–$C_6$-alkoxy groups such as methoxy, ethoxy, n-propoxy, isopropoxy, n-butoxy, isobutoxy, sec-butoxy, tert-butoxy, n-pentoxy, isopentoxy, n-hexoxy and isohexoxy, particularly preferably methoxy, ethoxy, n-propoxy and n-butoxy;

$C_6$–$C_{14}$-aryloxy groups such as phenoxy, ortho-cresyloxy, meta-cresyloxy, para-cresyloxy, α-naphthoxy, β-naphthoxy and 9-anthryloxy;

silyl groups $SiR^5R^6R^7$, where $R^5$ to $R^7$ are selected independently from among hydrogen, $C_1$–$C_8$-alkyl groups, the benzyl radical and $C_6$–$C_{14}$-aryl groups; preference is given to the trimethylsilyl, triethylsilyl, triisopropylsilyl, diethylisopropylsilyl, dimethylhexylsilyl, tert-butyldimethylsilyl, tert-butyldiphenylsilyl, tribenzylsilyl, triphenylsilyl and tri-para-xylylsilyl groups; particular preference is given to the trimethylsilyl group and the tert-butyldimethylsilyl group;

silyloxy groups $OSiR^5R^6R^7$, where $R^5$ to $R^7$ are selected independently from among hydrogen, $C_1$–$C_8$-alkyl groups, the benzyl radical and $C_6$–$C_{14}$-aryl groups; preference is given to the trimethylsilyloxy, triethylsilyloxy, triisopropylsilyloxy, diethylisopropylsilyloxy, dimethylhexylsilyloxy, tert-butyldimethylsilyloxy, tert-butyldiphenylsilyloxy, tribenzylsilyloxy, triphenylsilyloxy and tri-para-xylylsilyloxy groups; particular preference is given to the trimethylsilyloxy group and the tert-butyldimethylsilyloxy group.

It is preferred that at least one of the radicals $R^4$ and $R^{4*}$ is not hydrogen. In a particularly preferred embodiment, $R^1$ or $R^4$ is not hydrogen.

$R^2$ is $C_6$–$C_{14}$-aryl, unsubstituted or substituted by one or more identical or different substituents, or a five- to six-membered nitrogen-containing heteroaryl radical, unsubstituted or substituted by one or more identical or different substituents, where the substituents are as defined above.

$R^3$ and $R^8$ are identical or different and are selected from among $C_1$–$C_{18}$-alkyl, $C_2$–$C_{18}$-alkenyl, substituted or unsubstituted and having from one to 4 isolated or conjugated double bonds, $C_3$–$C_{12}$-cycloalkyl, substituted or unsubstituted, $C_7$–$C_{13}$-aralkyl, $C_6$–$C_{14}$-aryl, unsubstituted or substituted by one or more identical or different substituents, and five- and six-membered nitrogen-containing heteroaryl radicals, unsubstituted or substituted by one or more identical or different substituents, where the substituents are as defined above.

In a particularly preferred embodiment, $R^1$ is 2,6-diisopropylphenyl.

In a particularly preferred embodiment, $R^2$ is phenyl.

$L^1$ is selected from among uncharged, inorganic and organic ligands, for example from among phosphines of the formula $(R^8)_xPH_{3-x}$ or amines of the formula $(R^8)_xNH_{3-x}$, where x is an integer from 0 to 3. However, ethers $(R^8)_2O$ such as dialkyl ethers, e.g. diethyl ether, or cyclic ethers, for example tetrahydrofuran, $H_2O$, alcohols $(R^8)OH$ such as methanol or ethanol, pyridine, pyridine derivatives of the formula $C_5H_{5-x}(R^8)_xN$, for example 2-picoline, 3-picoline, 4-picoline, 2,3-lutidine, 2,4-lutidine, 2,5-lutidine, 2,6-lutidine or 3,5-lutidine, CO, $C_1$–$C_{12}$-alkylnitriles or $C_6$–$C_{14}$-arylnitriles, e.g. acetonitrile, propionitrile, butyronitrile or benzonitrile, are also suitable. Furthermore, singly or multiply ethylenically unsaturated double bond systems, e.g. ethenyl, propenyl, cis-2-butenyl, trans-2-butenyl, cyclohexenyl or norbornenyl, can serve as ligand.

In a particular embodiment, adjacent radicals $R^1$ to $R^4$ or $R^{4*}$ in the complexes of the formula I may be joined to one another to form a 5- to 12-membered ring. For example, $R^3$ and $R^4$ may together be: —$(CH_2)_3$— (trimethylene), —$(CH_2)_4$— (tetramethylene), —$(CH_2)_5$— (pentamethylene), —$(CH_2)_6$— (hexamethylene), —$CH_2$—CH=CH—, —$CH_2$—CH=CH—$CH_2$—, —CH=CH—CH=CH—, —O—$CH_2$—O—, —O—CHMe—O—, —O—CH—$(C_6H_5)$—O—, —O—$CH_2$—$CH_2$—O—, —O—$CMe_2$—O—, —NMe—$CH_2$—$CH_2$—NMe—, —NMe—$CH_2$—NMe— or —O—$SiMe_2$—O— where Me=$CH_3$.

The complexes of the present invention can be synthesized readily.

The synthesis of the novel complexes of the formula I generally starts out from a ligand of the formula II,

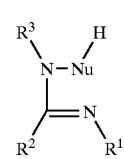

II where the variables are as defined above.

The ligands of the formula II are reacted with metal compounds of the formula $MX_2$. Here, $MX_2$ may optionally be stabilized by uncharged ligands. Possible uncharged ligands are the customary ligands of coordination chemistry, for example cyclic and noncyclic ethers, amines, diamines, nitriles, isonitriles or phosphines. Particular preference is given to diethyl ether, tetrahydrofuran, 1,2-dimethoxyethane, tetramethylethylenediamine, acetonitrile or triphenylphosphine.

The reaction is carried out in the absence of acids and bases by simple mixing in a solvent. Solvents which have been found to be useful are benzene, toluene, ortho-xylene, meta-xylene, para-xylene, ethylbenzene or mixtures thereof, also noncyclic or cyclic ethers such as 1,2-dimethoxyethane, tetrahydrofuran or diethyl ether, as well as chlorinated hydrocarbons such as methylene chloride or chloroform.

An appropriate temperature range is from −100° C. to +150° C., preferably from −78° C. to +100° C. The reaction temperature should not be below the melting point of the solvent; temperatures above the boiling point of the solvent concerned can be achieved in autoclaves. The reaction is preferably carried out in the absence of oxygen and moisture.

Suitable molar ratios of ligand to M are in the range from 5:1 to 1:5. However, since the ligands of the formula II are generally the more difficult-to-obtain reactants, molar ratios of ligand:M in the range from 1:1 to 1:3 are preferred, and particular preference is given to stoichiometric amounts.

The novel complexes of the formula I a are purified by the methods customary in organometallic chemistry, with particular preference being given to crystallization and precipitation. Filtration through filter aids such as Celite® is also useful.

The preparation of the ligands of the formula II is known per se and can be particularly readily carried out by reacting an amide of the formula III,

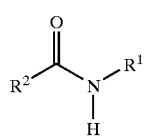

III which bears an acidic α-H atom on the nitrogen, with a halogenating agent such as SO$_2$Cl$_2$, PCl$_3$ or POCl$_3$ and subsequently reacting the product with a nucleophilic compound of the formula IV,

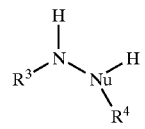

IV where the variables in the compounds III and IV are as defined above, in the presence of a base.

Preferred bases are tertiary amines such as triethylamine, diisopropylethylamine or pyridine. Solvents which have been found to be useful are alcohols or chlorinated hydrocarbons, for example methylene chloride or chloroform, or mixtures thereof, also noncyclic or cyclic ethers such as 1,2-dimethoxyethane, tetrahydrofuran or diethyl ether.

This reaction is generally complete after a period of from a few minutes to a few hours; a reaction time of from 30 minutes to 10 hours is useful and preference is given to from 1 to 5 hours. The temperature conditions are generally not critical; a temperature range from −90° C. to +30° C. is preferred, in exceptional cases up to 50° C.

The reaction is preferably carried out in the absence of oxygen and moisture.

Suitable molar ratios of III to IV are in the range from 5:1 to 1:5; preference is given to molar ratios of III:IV in the range from 3:1 to 1:3, and stoichiometric amounts are particularly preferred.

It has been found that the novel complexes of the formula I are suitable for polymerizing olefins. They polymerize and copolymerize ethylene and propylene particularly readily to form high molecular weight polymers.

For the novel complexes of the formula I to be catalytically active, they have to be activated. Suitable activators for the complexes of the formula I are selected aluminum or boron compounds bearing electron-withdrawing radicals (e.g. trispentafluorophenylboran, trispentafluorophenylaluminum, N,N-dimethylanilinium tetrakispentafluorophenylborate, tri-n-butylammonium tetrakispentafluorophenylborate, N,N-dimethylanilinium tetrakis(3,5-bisperfluoromethylphenyl)borate, tri-n-butylammonium tetrakis(3,5-bisperfluoromethylphenyl) borate and tritylium tetrakispentafluorophenylborate). Preference is given to dimethylanilinium tetrakispentafluorophenylborate, tritylium tetrakispentafluorophenylborate and trispentafluorophenylborane.

If boron or aluminum compounds are used as activators for the complexes of the present invention, they are generally used in a molar ratio to M of from 1:10 to 10:1, preferably from 1:2 to 5:1 and particular preferably in stoichiometric amounts.

Another useful class of activators consists of aluminoxanes. The structure of the aluminoxanes is not known precisely. They are products which are obtained by careful partial hydrolysis of aluminum alkyls (cf. DE-A 30 07 725). These products are not pure single compounds, but mixtures of open-chain and cyclic structures of the formulae V a and V b. These mixtures are presumably present in a dynamic equilibrium with one another.

In the formulae Va and Vb,

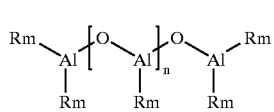

Va

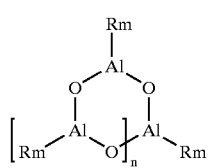

Vb the radicals R$^m$ are each, independently of one another

C$_1$–C$_{12}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, n-nonyl, n-decyl or n-dodecyl; preferably C$_1$–C$_6$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, particularly preferably methyl;

C$_3$–C$_{12}$-cycloalkyl such as cyclopropyl, cyclobutyl, cyclopentyl, cyclohexyl, cycloheptyl, cyclooctyl, cyclononyl, cyclodecyl, cycloundecyl or cyclododecyl; preferably cyclopentyl, cyclohexyl or cycloheptyl;

C$_7$–C$_{20}$-aralkyl, preferably C$_7$–C$_{12}$-phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl or 4-phenylbutyl, particularly prefearbly benzyl, or C$_6$–C$_{14}$-aryl such as phenyl, 1-naphthyl, 2-naphthyl, 1-anthryl, 2-anthryl, 9-anthryl, 1-phenanthryl, 2-phenanthryl, 3-phenanthryl, 4-phenanthryl or 9-phenanthryl, preferably phenyl, 1-naphthyl or 2-naphthyl, particularly preferably phenyl; and n is an integer from 0 to 40, preferably from 1 to 25 and particularly preferably from 2 to 22.

Cage-like structures for aluminoxanes are also discussed in the literature (Y. Koide, S. G. Bott, A. R. Barron *Organometallics* 1996, 15, 2213–26; A. R. Barron *Macromol. Symp.* 1995, 97, 15–25). Regardless of the actual structure of the aluminoxanes, they are suitable as activators for the novel metal complexes of the formulae I a and I b.

Mixtures of various aluminoxanes are particularly preferred activators in cases in which the polymerization is carried out in solution in a paraffin, for example n-heptane or isododecane. A particularly preferred mixture is the commercially available CoMAO of the formula $[(CH_3)_{0.9}(isoC_4H_9)_{0.1}AlO]_n$ obtainable from Witco GmbH.

To activate the complexes of the formula I by means of aluminoxanes, an excess of aluminoxane over M is generally necessary. Practical molar ratios of M:Al are in the range from 1:10 to 1:10000, preferably from 1:50 to 1:1000 and particularly preferably from 1:100 to 1:500.

The chosen complex of the formula I and the activator together form a catalyst system.

Addition of further aluminum alkyl of the formula $Al(R''')_3$ or aluminoxanes can increase the activity of the catalyst system of the present invention; aluminum alkyls of the formula $Al(R''')_3$ or aluminoxanes can also act as molar mass regulators. A further effective molar mass regulator is hydrogen. The molar mass can be regulated particularly effectively by means of the reaction temperature and the pressure. If the use of a boron compound as described above is desired, the addition of an aluminum alkyl of the formula $Al(R''')_3$ is particularly preferred.

Pressure and temperature conditions during the polymerization can be selected within wide limits. A pressure range which has been found to be useful is from 0.5 bar to 4000 bar, preferably from 10 to 75 bar or high-pressure conditions of from 500 to 2500 bar. A useful temperature range has been found to be from 0 to 120° C., preferably from 40 to 100° C. and particularly preferably from 50 to 85° C.

Suitable monomers include the following olefins: ethylene, propylene, 1-butene, 1-pentene, 1-hexene, 1-octene, 1-decene and 1-undecene, with propylene and ethylene being preferred and ethylene being particularly preferred. A further suitable monomer is styrene.

Suitable comonomers include α-olefins, for example from 0.1 to 20 mol % of 1-butene, 1-pentene, 1-hexene, 4-methyl-1-pentene, 1-octene, 1-decene or 1-undecene. However, isobutene and styrene are also suitable comonomers, also internal olefins such as cyclopentene, cyclohexene, norbornene and norbornadiene, or from 0.1 to 50 mol % of carbon monoxide.

Apart from other α-olefins, for example propene, 1-butene, 1-hexene, 1-octene or 1-decene, as comonomers, polar comonomers can also be incorporated with the aid of the catalyst system of the present invention. From 0.1 to 50 mol % of comonomer can be used. Preference is given to acrylates such as acrylic acid, methyl acrylate, ethyl acrylate, 2-ethylhexyl acrylate, n-butyl acrylate or tert-butyl acrylate;

methacrylic acid, methyl methacrylate, ethyl methacrylate, n-butyl methacrylate or tert-butyl methacrylate;

vinylaromatic compounds such as styrene;

vinyl carboxylates, with vinyl acetate being particularly preferred, unsaturated dicarboxylic acids, particularly preferably maleic acid, unsaturated dicarboxylic acid derivatives, particularly preferably maleic anhydride and alkylimides of maleic acid, for example maleic acid methylimide.

Furthermore, terpolymers comprising at least 2 of the abovementioned monomers together with ethylene can also be prepared.

Solvents which have been found to be useful are toluene, ortho-xylene, meta-xylene, para-xylene or ethylbenzene and mixtures thereof, also, under high-pressure conditions, supercritical ethylene.

The catalyst systems of the present invention polymerize olefins to give polyolefins having a very high molecular weight.

The polymerization using the catalyst systems of the present invention can be regulated by means of hydrogen, i.e. addition of hydrogen enables the molecular weight of the polymers obtainable by means of the catalyst system of the present invention to be reduced. If sufficient hydrogen is added, polyolefin waxes are obtained. The preferred concentration of the hydrogen is also dependent upon the type of polymerization plant employed.

For the catalyst systems of the present invention to be able to be used in modern polymerization processes such as suspension processes, bulk polymerization processes or gas-phase processes, it is necessary for them to be immobilized on a solid support. Otherwise, problems with polymer morphology (lumps, deposits on walls, blockages in lines or heat exchangers) can occur and force shutdown of the plant. Such an immobilized catalyst system is referred to as catalyst.

The catalyst systems of the present invention can be deposited on solid support materials. Suitable support materials are, for example, porous metal oxides of metals of groups 2 to 14 or mixtures thereof, also sheet silicates and zeolites. Preferred examples of metal oxides of groups 2 to 14 are $SiO_2$, $B_2O_3$, $Al_2O_3$, MgO, CaO and ZnO. Preferred sheet silicates are montmorillonites or bentonites; a preferred zeolite is MCM-41.

Particularly preferred support materials are spherical silica gels and aluminosilicate gels of the formula $SiO_2$ a $Al_2O_3$, where a is generally in the range from 0 to 2, preferably from 0 to 0.5. Such silica gels are commercially available, e.g. silica gel SG 332, Sylopol® 948 or 952 or S 2101 from W. R. Grace or ES 70X from Crosfield.

As particle size of the support materials, mean particle diameters of from 1 to 300 μm, preferably from 20 to 80 μm, have been found to be useful, with the particle diameter being determined by known methods such as sieve methods. The pore volume of the supports is from 1.0 to 3.0 ml/g, preferably from 1.6 to 2.2 ml/g and particularly preferably from 1.7 to 1.9 ml/g. The BET surface area is from 200 to 750 m$^2$/g, preferably from 250 to 400 m$^2$/g.

To remove impurities, in particular moisture, adhering to the support material, the support materials can be baked out, e.g. at from 45 to 1000° C., prior to doping. Temperatures of from 100 to 750° C. are particularly suitable for silica gels and other metal oxides. This baking can be carried out from a period of from 0.5 to 24 hours, preferably from 1 to 12 hours. The pressure conditions are dependent on the process chosen; baking can be carried out in a fixed bed, in a stirred vessel or else in a moving bed. Baking can generally be carried out at atmospheric pressure. However, reduced pressures of from 0.1 to 500 mbar are advantageous, a pressure range from 1 to 100 mbar is particularly advantageous and a range from 2 to 20 mbar is very particularly advantageous. On the other hand, moving-bed processes are advantageously carried out at slightly superatmopsheric pressure in the range from 1.01 bar to 5 bar, preferably from 1.1 to 1.5 bar.

Chemical pretreatment of the support material with an alkyl compound such as an aluminum alkyl, lithium alkyl or an aluminoxane is likewise possible.

A polymerization by the suspension method is carried out using suspension media in which the desired polymer is insoluble or only slightly soluble, because otherwise deposits of the product occur in plant components in which the product is separated from the suspension medium and force repeated shutdowns and cleaning operations. Suitable suspension media are saturated hydrocarbons such as propane, n-butane, isobutane, n-pentane, isopentane, n-hexane, isohexane and cyclohexane, with isobutane being preferred.

Pressure and temperature conditions during the polymerization can be selected within wide limits. A useful pressure range has been found to be from 0.5 bar to 150 bar, preferably from 10 to 75 bar. A useful temperature range has been found to be from 0 to 120° C., preferably from 40 to 100° C.

Suitable monomers include the following olefins: ethylene, propylene, 1-butene, 1-pentene, 1-hexene, 1-octene, 1-decene and 1-undecene.

Suitable comonomers include α-olefines, for example from 0.1 to 20 mol % of 1-butene, 1-pentene, 1-hexene, 4-methyl-1-pentene, 1-octene, 1-decene or 1-undecene. However, isobutene and styrene are also suitable comonomers, also internal olefins such as cyclopentene, cyclohexene, norbornene and norbornadiene. From 0.1 to 50 mol % of carbon monoxide is also suitable.

The catalysts of the present invention have an overall property profile which is advantageous in process engineering terms.

Furthermore, hydrogen has been found to be useful as chain transfer agent in polymerizations using the catalysts of the present invention, i.e. the molecular weight of the polymers obtainable by means of the catalyst of the present invention can be reduced by addition of hydrogen. If sufficient hydrogen is added, waxes are obtained; the hydrogen concentration required also depending on the type of polymerization plant employed. The addition of hydrogen generally increases the activity of the catalysts of the present invention.

The catalysts of the present invention can also be used together with one or more polymerization catalysts known per se. Thus, they can, for example, be used together with
  Ziegler-Natta catalysts,
  supported metallocene catalysts containing transition metals of groups 4 to 6 of the Periodic Table of the Elements,
  catalysts containing late transition metals (WO 96/23010),
  Fe or Co complexes with pyridyldiimine ligands as are disclosed in WO 98/27124,
  or chromium oxide catalysts of the Phillips type.

It is possible to mix various catalysts with one another and meter them in together or to use cosupported complexes on a common support or to meter various catalysts separately into the polymerization vessel at the same place or at different places.

The following examples illustrate the invention.

General Preliminary Remarks:

All work was, unless indicated otherwise, carried out with exclusion of air and moisture using standard Schlenk techniques. Apparatus and chemicals were prepared appropriately. The polymer viscosity was determined in accordance with ISO 1628-3.

1. Preparation of the Ligands
1.1. Preparation of Ligand II.1

The synthesis of the protonated ligands is illustrated by way of example by the description of the synthesis of II.1.

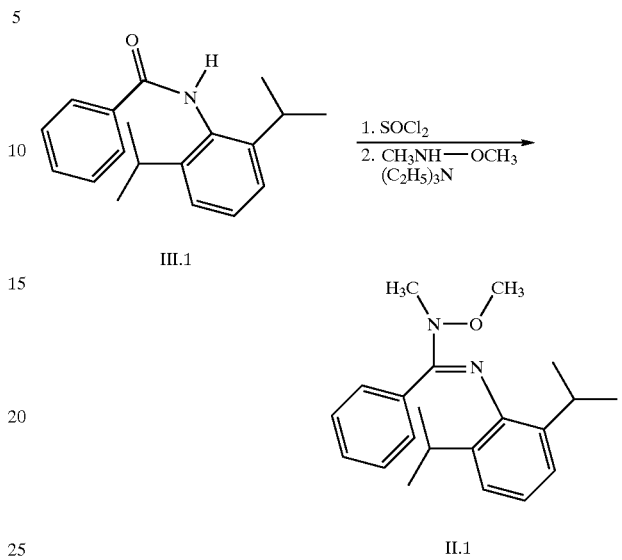

a) 1.98 g of N-(2,6-diisopropylphenyl)benzamide (7.0 mmol) III.1 were placed in a dry Schlenk tube which had been flushed with argon. After addition of 10 ml of thionyl chloride (137 mmol), the reaction solution was refluxed for 60 minutes. Excess $SOCl_2$ was distilled off under a high vacuum, and the yellow oil which remained was dissolved in 20 ml of methylene chloride (absolute).

b) The yellow N,O-dimethylhydroxylamine hydrochloride (0.78 g, 8.0 mmol) was placed in a baked-out Schlenk tube which had been flushed with argon, dissolved in absolute ethanol (50 ml) and activated with 2.2 ml of triethylamine (16 mmol).

The imide chloride III.1 prepared as described in a) and dissolved in methylene chloride was added slowly from a dropping funnel to the solution b) at −45° C. over a period of 45 minutes. After warming to room temperature, the reaction solution was stirred for 1 hour (color change: greenish→lemon yellow). Subsequent thin layer chromatography (diethyl ether/n-hexane=1/1) was no longer able to detect any III.1.

The reaction solution was poured into water (about 100 ml) and the product was extracted 3 times with 50 ml each time of diethyl ether. The combined organic phases were dried over $Na_2SO_4$ and the dessicant was filtered off. After the solvent had been taken off on a rotor evaporator, the resulting viscous oil was dried in a high vacuum.

Yield: 2.11 g (93%), empirical formula: $C_{21}H_{28}N_2O$, color: brown $^1$H-NMR (CDCl$_3$): 0.91 (6H, d, CH(C$\underline{H}_3$)$_2$, J=7.0 Hz), 1.06 (6H, d, CH(C$\underline{H}_3$)$_2$, J=7.0 Hz), 2.89 (2H, sept, 2×C$\underline{H}$(CH$_3$)$_2$, J=7.0 Hz), 3.15 (3H, s, N—CH$_3$), 3.49 (3H, s, O—CH$_3$), 6.82–6.89 (3H, m, phenyl), 7.13 (5H, s, phenyl).

$^{13}$C-NMR (CDCl$_3$): 21.9, 23.9 (CH($\underline{C}$H$_3$)$_2$), 28.0 ($\underline{C}$H(CH$_3$)$_2$), 37.0 (N—CH$_3$), 60.2 (O—CH$_3$), 122.4, 122.5, 127.5, 128.1, 128.8 (C-phenyl), 137.1 (C=N-$\underline{C}$, quaternary C, phenyl), 144.0 (C=N).

IR (KBr, cm$^{-1}$): 2962 (m), 2931 (m), 1634 (vs), 1602 (m), 1590 (m), 1461 (m), 1436 (m), 1360 (w), 1324 (m), 1256 (w), 1181 (w), 1104 (m), 1057 (w), 1030 (w), 1007 (m), 778 (m), 760 (m), 722 (w), 700 (vs).

MS (EI): M$^+$=324.3 m/e

EXAMPLE 1.2

Preparation of Ligand II.2

The symmetrically substituted N,N'-dimethylhydrazine hydrochloride (0.55 g, 4.1 mmol) was placed in a baked-out Schlenk tube which had been flushed with argon and suspended in 20 ml of methylene chloride (abs.). The addition of 1.73 ml of triethylamine (12.4 mmol) resulted in a turbid, milky solution.

After the reaction solution had been cooled to −70° C., 10 ml of compound III.1 (stock solution, c=0.108 g/ml) were slowly added from a dropping funnel over a period of 30 minutes. The initially orange solution became yellow over a period of 5 minutes after removal of the cold bath. The N,N'-dimethylhydrazine went completely into solution, and the reaction was complete after 1 hour at room temperature, as demonstrated by thin layer chromatography.

The reaction solution was poured into water (about 100 ml), and the product was extracted 3 times with 50 ml each time of diethyl ether. To achieve better phase separation, 50 ml of saturated sodium chloride solution were added. The combined organic phases were dried over $Na_2SO_4$ and the dessicant was filtered off. After the solvent had been removed on a rotary evaporator, the resulting viscous oil was dried in a high vacuum. Attempts to precipitate the target product from ether/hexane mixtures failed, but an analytically pure, pulverulent, brown solid was obtained after taking off the solvent (firstly ether, then hexane) over a period of 30 minutes.

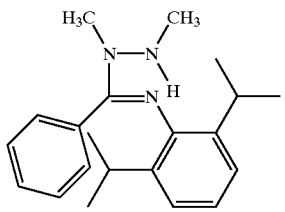

II.2

Yield: 1.10 g (94%), empirical formula: $C_{21}H_{29}N_2O$, color: brown $^1$H-NMR (CDCl$_3$): 0.94 (6H, d, CH(C$\underline{H}_3$)$_2$, J=7.0 Hz), 1.06 (6H, d, CH(CH$_3$)$_2$, J=6.6 Hz), 2.64 (3H, s, C$\underline{H}_3$—NH), 2.90 (3H, s, N—CH$_3$), 2.94 (2H, sept, 2×C$\underline{H}$(CH$_3$)$_2$), 6.78–6.86 (3H, m, phenyl), 7.01–7.14 (5H, m, phenyl).

$^{13}$C NMR (CDCl$_3$): 21.8, 24.1 (CH($\underline{C}$H$_3$)$_2$), 28.1 ($\underline{C}$H(CH$_3$)$_2$), 36.4 (NH—CH$_3$), 39.2 (N—CH$_3$), 122.1, 122.2, 127.8, 128.1, 128.8, 133.1, 138.2 (C-phenyl), 144.7 (C=N—$\underline{C}$, quaternary C, phenyl), 157.3 (C=N).

IR (KBr, cm$^{-1}$): 3244 (w), 3062 (w), 3022 (w), 2973 (m), 2960 (m), 1609 (vs), 1596 (s), 1586 (vs), 1576 (s), 1492 (w), 1439 (m), 1382 (m), 1364 (s), 1329 (m), 1262 (m), 1183 (w), 1111 (m), 1069 (s), 1046 (m), 1025 (s), 924 (m), 845 (s), 824 (m), 808 (w), 799 (m), 772 (vs), 760 (vs), 714 (vs), 700 (vs)

MS (EI): M$^+$=323.3 m/e

EXAMPLE 1.3

Preparation of Ligand II.3

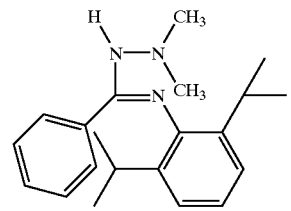

II.3

Commercial N,N-dimethylhydrazine (0.58 ml, 0.46 g, 7.7 mmol) was placed in a baked-out Schlenk tube which had been flushed with argon and was dissolved in absolute ethanol (50 ml).

The III.1 dissolved in methylene chloride (10 ml, 1.08 g, 3.6 mmol, c=0.115 g/ml) was slowly added at −45° C. from a dropping funnel over a period of 60 minutes. After warming to room temperature, the reaction solution was stirred for 1 hour (color change: colorless→yellow). The hydrazinium salt formed in the reaction precipitated and a turbid suspension was obtained. The reaction was monitored by thin layer chromatography (diethyl ether/hexane=1/1).

The reaction solution was poured into water (about 100 ml), and the product was extracted 3 times with 50 ml each time of diethyl ether. The combined organic phases were dried over $Na_2SO_4$ and the dessicant was filtered off. After the solvent had been taken off on a rotary evaporator, the resulting viscous oil was dried in a high vacuum.

Yield: 1.15 g (99%), empirical formula: $C_{21}H_{29}N_3$, color: brown $^1$H-NMR (CDCl$_3$): 0.88 (6H, d, CH(C$\underline{H}_3$)$_2$, J=6.9 Hz), 1.10 (6H, d, CH(C$\underline{H}_3$)$_2$, J=6.9 Hz), 2.57 (6H, s, N(C$\underline{H}_3$)$_2$), 3.13 (2H, sept, 2×C$\underline{H}$(CH$_3$)$_2$, J=6.9 Hz), 6.98 (2H, pseudo-d, phenyl), 7.07–7.21 (6H, m, phenyl), 7.95 (1H, s, N—H)

$^{13}$C-NMR (CDCl$_3$): 21.9, 24.9 (CH($\underline{C}$H$_3$)$_2$), 26.3 ($\underline{C}$H(CH$_3$)$_2$), 46.7 (N($\underline{C}$H$_3$)$_2$), 123.3, 126.9, 127.6, 128.5, 129.1 (C-phenyl), 132.9, 134.3 (aniline-C(2,6), quaternary C), 145.2 (C=N—C, quaternary C, phenyl), 159.7 (C=N)

TABLE 1

Overview of the ligands of the formula II

| Compound | R$^1$ | R$^2$ | R$^3$ | R$^4$ | Nu |
|---|---|---|---|---|---|
| II.1 | 2,6-(i-C$_3$H$_7$)$_2$C$_6$H$_3$ | C$_6$H$_5$ | CH$_3$ | CH$_3$ | O |
| II.2 | 2,6-(i-C$_3$H$_7$)$_2$C$_6$H$_3$ | C$_6$H$_5$ | CH$_3$ | CH$_3$ | N—H |
| II.3 | 2,6-(i-C$_3$H$_7$)$_2$C$_6$H$_3$ | C$_6$H$_5$ | CH$_3$ | H | N—CH$_3$ | i-C$_3$H$_7$: isopropyl

2. Syntheses of Complexes of the Formula I 2.1. Synthesis of the Complex I.1

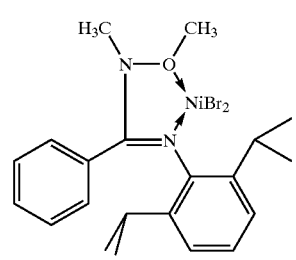

I.1

In a baked-out Schlenk tube which had been flushed with argon, the ligand II.1 (0.97 g, 3.0 mmol) was dissolved in 20 ml of methylene chloride (absolute), and, after addition of the dimethoxyethane-stabilized transition metal halide (NiBr$_2$×2 DME, 1.25 g, 3.1 mmol), the mixture was stirred at room temperature. The following color changes were observed: yellowish→turbid orange (after 10 s)→turbid brown (after ½ min)→turbid green. After 10 minutes, a dark green suspension whose color remained unchanged even after stirring for 48 hours was obtained.

After addition of 60 ml of methylene chloride (absolute), the slight excess of unreacted NiBr$_2$×2 DME was separated off by filtration (G4 frit, without Celite®). The clear, dark green filtrate was evaporated to dryness in a high vacuum. A pulverulent green complex I.1 was isolated.

Yield: 1.53 g (94%), empirical formula: C$_{21}$H$_{28}$Br$_2$N$_2$NiO, color: green $^1$H-NMR (CD$_2$Cl$_2$): weakly paramagnetic, 1.10–1.49 (12H, m, 2×CH(C$\underline{H}_3$)$_2$), 2.97–3.56 (8H, m, 2×C$\underline{H}$(CH$_3$)$_2$, N—C$\underline{H}_3$, O—C$\underline{H}_3$)

EXAMPLE 2.2

Synthesis of the Complex I.2

Example 2.1 was repeated using the ligand II.2

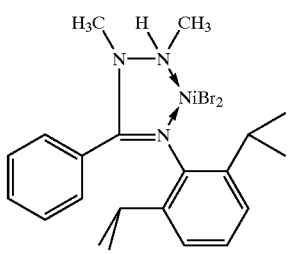

Yield: 0.70 g (95%), empirical formula: C$_{21}$H$_{29}$Br$_2$N$_3$Ni, color: beige 1H-NMR (CD$_2$Cl$_2$): 1.76, 5.16, 5.41, 15.38, 19.63, 22.57, compound is paramagnetic and no assignment can be made.

EXAMPLE 2.3.

Synthesis of the Complex I.3

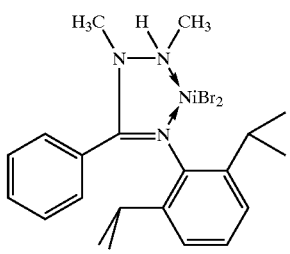

Example 2.1 was repeated using ligand II.3

Yield: 0.66 g (76%), empirical formula: C$_{21}$H$_{29}$Br$_2$N$_3$Ni, color: beige $^1$H-NMR (CD$_2$Cl$_2$): 0.89–2.04 (12H, m, 2×CH(C$\underline{H}_3$)$_2$), 3.48 (2H, s, broad, 2×C$\underline{H}$(CH$_3$)$_2$), 6,00 (6H, s, broad, N(CH$_3$)$_2$), 7,11–8,96 (8H, m, phenyl). The signals are broad and shifted to low field. The complex is slightly paramagnetic.

$^{13}$C-NMR (CD$_2$Cl$_2$): 13.1, 21.8, 22.2, 24.7, 29.8, 30.7 (CH($\underline{C}$H$_3$)$_2$, $\underline{C}$H(CH$_3$)$_2$), 50.8 (N—CH$_3$), 124.0, 126.0, 127.7, 129.7, 131.2, 131.7, 135.5 (C-phenyl), 140.0 (C=N—C, quaternary $\underline{C}$, phenyl), 143.8 (C=N).

TABLE 2

Overview of the novel complexes of the formula I

| Compound | R$^1$ | R$^2$ | R$^3$ | R$^4$ | Nu | X | M |
|---|---|---|---|---|---|---|---|
| I a.1 | 2,6-(i-C$_3$H$_7$)$_2$C$_6$H$_3$ | C$_6$H$_5$ | CH$_3$ | CH$_3$ | O | Br | Ni |
| I a.2 | 2,6-(CH$_3$)$_2$C$_6$H$_3$ | C$_6$H$_5$ | CH$_3$ | CH$_3$ | N—H | Br | Ni |
| I a.3 | 2-(C$_6$H$_5$)—C$_6$H$_4$ | C$_6$H$_5$ | CH$_3$ | H | N—CH$_3$ | Br | Ni | i-C$_3$H$_7$: isopropyl; p-CH$_3$—C$_6$H$_4$: para-tolyl

3. Polymerization Experiments 3.1. Polymerization in an Autoclave

The indicated amount of the complex to be examined, 2 ml of 30% strength by weight MAO solution in toluene (commercially available from Witco) and 400 ml of toluene were placed in a 1 l steel autoclave which had been made inert. At 70° C., the autoclave was pressurized with ethylene to a pressure of 40 bar. This pressure was kept constant over the 90 minutes of the test by metering in further amounts of ethylene. The reaction was stopped by venting and the polymer was isolated by filtration, subsequent washing with methanol and drying under reduced pressure.

TABLE 3

Polymerization results

Ethylene polymerization (40 bar)

| Complex | Activity [gmmol$^{-1}$h$^{-1}$bar$^{-1}$] | Yield [g] | η [dl/g] | Time [min] | Weight of complex used [mg] |
|---|---|---|---|---|---|
| I.1 | 302.8 | 7.25 | 3.62 | 5 | 3.9 |
| I.2 | 3.3 | 1.0 | 2.15 | 90 | 2.7 |
| I.3 | 8.4 | 1.3 | 2.57 | 90 | 1.4 |

3.3 Ethylene/hexene copolymerization

The procedure of 3.1 was repeated but 12.5 ml of 1-hexene were added to the autoclave at the beginning together with the other reagents.

TABLE 4

Copolymerization results

Copolymerization (ethene/hexene, 40 bar)

| Complex | 1-Hexene addition [ml] | Activity [gmmol$^{-1}$h$^{-1}$bar$^{-1}$] | Yield [g] | η [dl/g] | Time [min] | Weight of complex used [mg] |
|---|---|---|---|---|---|---|
| I.1 | 12.5 | 1.8 | 0.7 | — | 90 | 3,6 |

We claim:
1. A complex of the formula I,

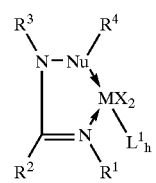

wherein
Nu is selected from the group consisting of O, S, N—R$^4$*, and P-R$^4$*;

M is Ni or Pd;

h is an integer from 0 to 4;

X are the same or different and are selected from the group consisting of a halogen, $C_1$–$C_8$-alkyl, $C_3$–$C_{12}$-cycloalkyl, $C_7$–$C_{13}$-aralkyl and $C_6$–$C_{14}$-aryl, $R^1$, $R^4$, $R^{4*}$ are the same or different and are selected from the group consisting of hydrogen, substituted or unsubstituted $C_1$–$C_{18}$-alkyl, substituted or unsubstituted $C_2$–$C_{18}$-alkenyl comprising from one to 4 isolated or conjugated double bonds and is bound via a single bond, substituted or unsubstituted $C_3$–$C_{12}$-cycloalkyl, $C_7$–$C_3$-aralkyl, unsubstituted or substituted $C_6$–$C_{14}$-aryl, and unsubstituted or substituted five- to six-membered nitrogen-containing heteroaryl radicals which are bound via a single bond;

$R^2$ is an unsubstituted or substituted $C_6$–$C_{14}$-aryl, or an unsubstituted or substituted five- to six-membered nitrogen-containing heteroaryl radical;

$R^3$, $R^8$ are each selected from the group consisting of $C_1$–$C_{18}$-alkyl, substituted or unsubstituted $C_2$–$C_{18}$-alkenyl comprising from one to 4 isolated or conjugated double bonds, substituted or unsubstituted $C_3$–$C_{12}$-cycloalkyl, $C_7$–$C_{13}$-aralkyl, unsubstituted or substituted $C_6$–$C_{14}$-aryl, or a unsubstituted or substituted five- to six-membered nitrogen-containing heteroaryl radical;

wherein adjacent radicals $R^1$ to $R^4$ or $R^{4*}$ may be joined to one another to form a 5- to 12-membered ring which may comprise a substituent selected from the group consisting of substituted or unsubstituted $C_1$–$C_8$-alkyl, substituted or unsubstituted $C_2$–$C_8$-alkenyl comprising from one to 4 isolated or conjugated double bonds, substituted or unsubstituted $C_3$–$C_{12}$-cycloalkyl, $C_7$–$C_{13}$-aralkyl, and $C_6$–$C_{14}$-aryl;

$L^1$ is an uncharged, organic or inorganic ligand.

2. The complex as claimed in claim 1, wherein Nu is oxygen, M is Ni and X is halogen and $L^1$ is selected from the group consisting of phosphines $(R^8)_x PH_{3-x}$, amines $(R^8)_x NH_{3-x}$, ethers $(R^8)_2 O$, $H_2O$, alcohols $(R^8)OH$, pyridine, pyridine derivatives of the formula $C_5H_{5-x}(R^8)_x N$, CO, $C_1$–$C_{12}$-alkylnitriles, $C_6$–$C_{14}$-arylnitriles, and ethylenically unsaturated double bond systems, wherein x is an integer from 0 to 3; and $R^8$ are identical or different and are selected from the group consisting of $C_1$–$C_{18}$-alkyl, substituted or unsubstituted $C_2$–$C_{18}$-alkenyl comprising from one to 4 isolated or conjugated double bonds, substituted or unsubstituted $C_3$–$C_{12}$-cycloalkyl, $C_7$–$C_{13}$-aralkyl, unsubstituted or substituted $C_6$–$C_{14}$-aryl, and unsubstituted or substituted five- to six-membered nitrogen-containing heteroaryl radicals, wherein the substituents are the same or different and selected from the group consisting of $C_1$–$C_{18}$-alkyl, $C_2$–$C_{18}$-alkenyl, $C_3$–$C_{12}$-cycloalkyl, $C_7$–$C_{13}$-aralkyl, $C_6$–$C_{14}$-aryl, halogen, $C_1$–$C_6$-alkoxy, $C_6$–$C_{14}$-aryloxy, $SiR^5R^6R^7$ and $O$—$SiR^5R^6R^7$.

3. The complex as claimed in claim 1, wherein h is 0.

4. The complex as claimed in claim 3, wherein h is 0.

5. The complex as claimed in claim 1, wherein X is a halogen.

6. The complex as claimed in claim 1, wherein $R^1$ is 2,6-diisopropylphenyl.

7. The complex as claimed in claim 1, wherein $R^2$ is phenyl.

8. A composition comprising the complex as claimed in claim 1 immobilized on a solid support.

9. A composition comprising the complex as claimed in claim 2 immobilized on a solid support.

10. A composition comprising the complex as claimed in claim 3 immobilized on a solid support.

11. A composition comprising the complex as claimed in claim 4 immobilized on a solid support.

12. A composition comprising the complex as claimed in claim 5 immobilized on a solid support.

13. A composition comprising the complex as claimed in claim 6 immobilized on a solid support.

14. A composition comprising the complex as claimed in claim 7 immobilized on a solid support.

* * * * *